United States Patent
Levi et al.

(10) Patent No.: US 7,103,471 B2
(45) Date of Patent: Sep. 5, 2006

(54) MULTI-MODE NAVIGATION DEVICE AND METHOD

(75) Inventors: Robert W. Levi, Anaheim, CA (US); Charles T. Judd, Carlsbad, CA (US); Steven J. Davis, Hermosa Beach, CA (US)

(73) Assignee: Honeywell International Inc., Minneapolis, MN (US)

(*) Notice: Subject to any disclaimer, the term of this patent is extended or adjusted under 35 U.S.C. 154(b) by 26 days.

(21) Appl. No.: 10/664,176

(22) Filed: Sep. 17, 2003

(65) Prior Publication Data

US 2004/0059502 A1 Mar. 25, 2004

Related U.S. Application Data

(60) Provisional application No. 60/412,348, filed on Sep. 20, 2002.

(51) Int. Cl.
*G06G 7/78* (2006.01)
*G08B 29/02* (2006.01)

(52) U.S. Cl. .................. 701/200; 701/213; 235/105

(58) Field of Classification Search .............. 701/200, 701/213, 207, 216, 217, 300, 212, 211; 702/160; 33/319; 235/105; 73/865.4
See application file for complete search history.

(56) References Cited

U.S. PATENT DOCUMENTS

| | | |
|---|---|---|
| 2,091,964 A | 9/1937 | Carter |
| 3,583,074 A | 6/1971 | Baker et al. |
| 4,031,630 A | 6/1977 | Fowler |
| 4,143,467 A | 3/1979 | Erspamer et al. |
| 4,347,730 A | 9/1982 | Fisher et al. |
| 4,611,293 A | 9/1986 | Hatch et al. |
| 4,622,646 A | 11/1986 | Waller et al. |
| 4,656,750 A | 4/1987 | Pitt et al. |
| 4,809,007 A | 2/1989 | Hassenplug |
| 4,851,775 A | 7/1989 | Kim et al. |
| 4,887,081 A | 12/1989 | Iihoshi et al. |
| 4,991,126 A | 2/1991 | Reiter |
| 5,043,736 A * | 8/1991 | Darnell et al. ........... 342/357.1 |
| 5,067,083 A | 11/1991 | Nakayama et al. |
| 5,115,238 A | 5/1992 | Shimizu et al. |
| 5,122,960 A | 6/1992 | Ooka |
| 5,235,514 A | 8/1993 | Matsuzaki |
| 5,239,264 A | 8/1993 | Hawks |
| 5,287,295 A | 2/1994 | Ives et al. |
| 5,287,297 A | 2/1994 | Ihara et al. |

(Continued)

OTHER PUBLICATIONS

Ladetto, Quentin, et al., "Combining Gyroscopes, Magnetic Compass and GPS for Pedestrian Navigation", date unknown, Geodetic Engineering Laboratory, Institute of Geomatics, Swiss Institute of Technology, 8 pg.

(Continued)

*Primary Examiner*—Dalena Tran
(74) *Attorney, Agent, or Firm*—Sheldon & Mak PC

(57) ABSTRACT

A method and apparatus for providing dead reckoning position data, orientation, and heading of a person is disclosed. The apparatus uses an algorithm that automatically determines the appropriate set of navigation functions for personal navigation based upon the orientation of the apparatus. Dead reckoning is accomplished by combining electronic heading and motion signals from human ambulation. Individual orientation and human motion measurement is accomplished with motion sensing devices. In one implementation of the invention, a navigation device provides different heading, position, and/or orientation functionality depending on whether the navigation device is affixed to the user in a vertical position or horizontal position, or the navigation device is not affixed to the user.

19 Claims, 5 Drawing Sheets

U.S. PATENT DOCUMENTS

| | | | |
|---|---|---|---|
| 5,287,628 A | 2/1994 | Yamaguchi et al. | |
| 5,297,050 A | 3/1994 | Ichimura et al. | |
| 5,319,561 A | 6/1994 | Matsuzaki | |
| 5,327,348 A | 7/1994 | Kato | |
| 5,331,563 A | 7/1994 | Masumoto et al. | |
| 5,404,307 A | 4/1995 | Odagawa | |
| 5,424,953 A | 6/1995 | Masumoto et al. | |
| 5,428,902 A | 7/1995 | Cheah | |
| 5,488,788 A | 2/1996 | Durbin | |
| 5,583,776 A | 12/1996 | Levi et al. | |
| 5,731,757 A * | 3/1998 | Layson, Jr. | 340/573.1 |
| 5,935,191 A | 8/1999 | Sakanashi et al. | |
| 5,956,660 A | 9/1999 | Neumann | |
| 5,986,583 A | 11/1999 | Nakano et al. | |
| 6,018,705 A | 1/2000 | Gaudet et al. | |
| 6,032,099 A | 2/2000 | Fernandez | |
| 6,052,654 A | 4/2000 | Gaudet et al. | |
| 6,067,046 A | 5/2000 | Nichols | |
| 6,081,230 A | 6/2000 | Hoshino et al. | |
| 6,122,960 A | 9/2000 | Hutchings et al. | |
| 6,132,391 A | 10/2000 | Onari et al. | |
| 6,145,389 A | 11/2000 | Ebeling et al. | |
| 6,175,608 B1 | 1/2001 | Pyles et al. | |
| 6,204,807 B1 | 3/2001 | Odagiri et al. | |
| 6,243,660 B1 * | 6/2001 | Hsu et al. | 702/160 |
| 6,282,496 B1 | 8/2001 | Chowdhary | |
| 6,298,314 B1 | 10/2001 | Blackadar et al. | |
| 6,301,964 B1 | 10/2001 | Fyfe et al. | |
| 6,305,221 B1 | 10/2001 | Hutchings | |
| 6,366,855 B1 * | 4/2002 | Reilly et al. | 701/213 |
| 6,408,251 B1 | 6/2002 | Azuma | |
| 6,415,223 B1 | 7/2002 | Lin et al. | |
| 6,513,381 B1 | 2/2003 | Fyfe et al. | |
| 6,522,266 B1 * | 2/2003 | Soehren et al. | 340/988 |
| 6,546,336 B1 | 4/2003 | Matsuoka et al. | |
| 6,801,855 B1 * | 10/2004 | Walters et al. | 701/216 |
| 2001/0045128 A1 | 11/2001 | McCall et al. | |
| 2002/0040601 A1 | 4/2002 | Fyfe et al. | |
| 2002/0089425 A1 | 7/2002 | Kubo et al. | |
| 2002/0091482 A1 | 7/2002 | Eakle, Jr. et al. | |
| 2002/0111717 A1 | 8/2002 | Scherzinger et al. | |
| 2002/0128775 A1 | 9/2002 | Brodie et al. | |
| 2002/0143491 A1 | 10/2002 | Scherzinger | |
| 2003/0018430 A1 | 1/2003 | Ladetto et al. | |

OTHER PUBLICATIONS

Ladetto, Quentin, "On Foot Navigation: Continuous Step Calibrations Using Both Complementary Recursive Prediction and Adaptive Kalman Filtering", date unknown, Geodetic Laboratory, Institute of Geomatics, Swiss Federal Institute of Technology, 6 pg.

Gabaglio, Vincent et al., "Real-Time Calibration of LEngth of Steps with GPS and Accelerometers", Swiss Federal Institute of Technology, Geodetic Engineering Laboratory, 6 pg.

Ladetto, Quentin et al., "Digital Magnetic Compass and Gyroscope Integration for Pedestrian Navigation", Faculte ENAC, Institut du Developpment Territorial, Geodetic Laboratory, 10 pg.

\* cited by examiner

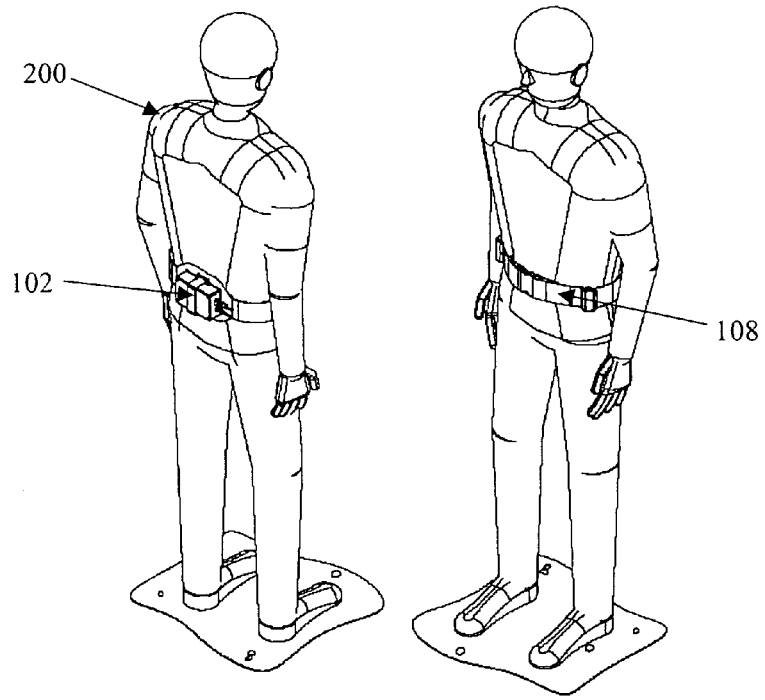
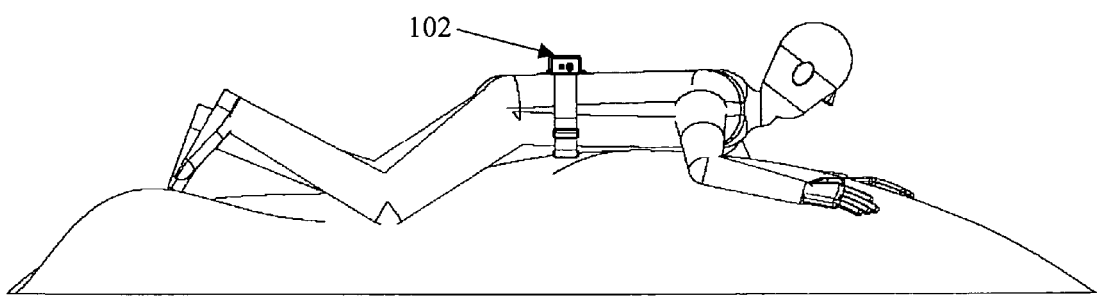
Figure 2  Figure 3
Figure 4

MULTI-MODE NAVIGATION DEVICE AND METHOD

CROSS REFERENCE TO RELATED APPLICATIONS

This non-provisional United States (U.S.) patent application claims the benefit of U.S. Provisional Application No. 60/412,348 filed on Sep. 20, 2002 by inventors Robert W. Levi, Charles T. Judd, and Steven J. Davis, titled "Multi-Mode Navigation Device and Method."

FIELD

Various embodiments of the invention pertain to navigation systems. More particularly, at least one embodiment of the invention relates to navigation devices that are handheld, attached, or worn by an individual for the purposes of geo-location, personal navigation, heading or bearing determination, and/or monitoring the orientation in space of an individual.

DESCRIPTION OF RELATED ART

U.S. Pat. No. 5,583,776 issued to Levi et al., describes a dead reckoning navigational system for personnel on foot using a motion sensing device, such as an accelerometer, to measure foot impacts. Dead reckoning is a method of deducing displacement in accordance with an object's motion, relative to a known point. Dead reckoning navigation for persons is typically based upon the stride length and heading of the user. Foot impact detection triggers an increment in position by the average stride distance of an individual, in the direction of the individual's heading.

Some patents describe compass-like devices having some limited potential for personal navigation, such as U.S. Pat. No. 4,656,750 issued to Pitt et al., in which a triad of Hall effect sensors and accelerometers are used to determine heading. Additionally, in U.S. Pat. No. 5,287,628 issued to Yamaguchi et al., an omni-range inclino-compass is described. These patents, however, do not describe any functionality beyond that which might be obtainable with a mechanically gimbaled compass. In U.S. Pat. No. 5,287,628 the emphasis is on an 'omni-range' compass functionality, with no translation detecting capability whatsoever and no change of function based upon orientation.

BRIEF DESCRIPTION OF THE DRAWINGS

FIGS. 2–4 illustrate a navigation device attached to a person that synchronizes its reference orientation with the orientation of the person.

DETAILED DESCRIPTION

In the following description numerous specific details are set forth in order to provide a thorough understanding of the invention. However, one skilled in the art would recognize that the invention may be practiced without these specific details. In other instances, well known methods, procedures, and/or components have not been described in detail so as not to unnecessarily obscure aspects of the invention.

In the following description, certain terminology is used to describe certain features of one or more embodiments of the invention. For instance, the term "dead reckoning" is used to refer to determining a location and distance of travel. The terms "heading" and "azimuth" are interchangeably used to refer to a fixed direction.

Generally, one aspect of an embodiment of the invention relates to a device that changes navigation functions based upon its orientation, and the method by which the navigation functions are selected and accomplished. In one implementation of the invention, a navigation device provides different heading, position, and/or orientation functionality depending on whether the navigation device is affixed to the user in a vertical position or horizontal position, or the navigation device is not affixed to the user.

A novel aspect of the invention provides a personal navigation device and a method of using the orientation of the personal navigation device to enable the navigation function of dead reckoning via pedometry. Also novel is the use of orientation as a basis for modifying the set of sensors, and algorithms used, for that pedometry. In this definition, pedometry also includes the detection of motion made if the user is in a crawling, or other non-upright, yet ambulatory mode.

Figure 1:
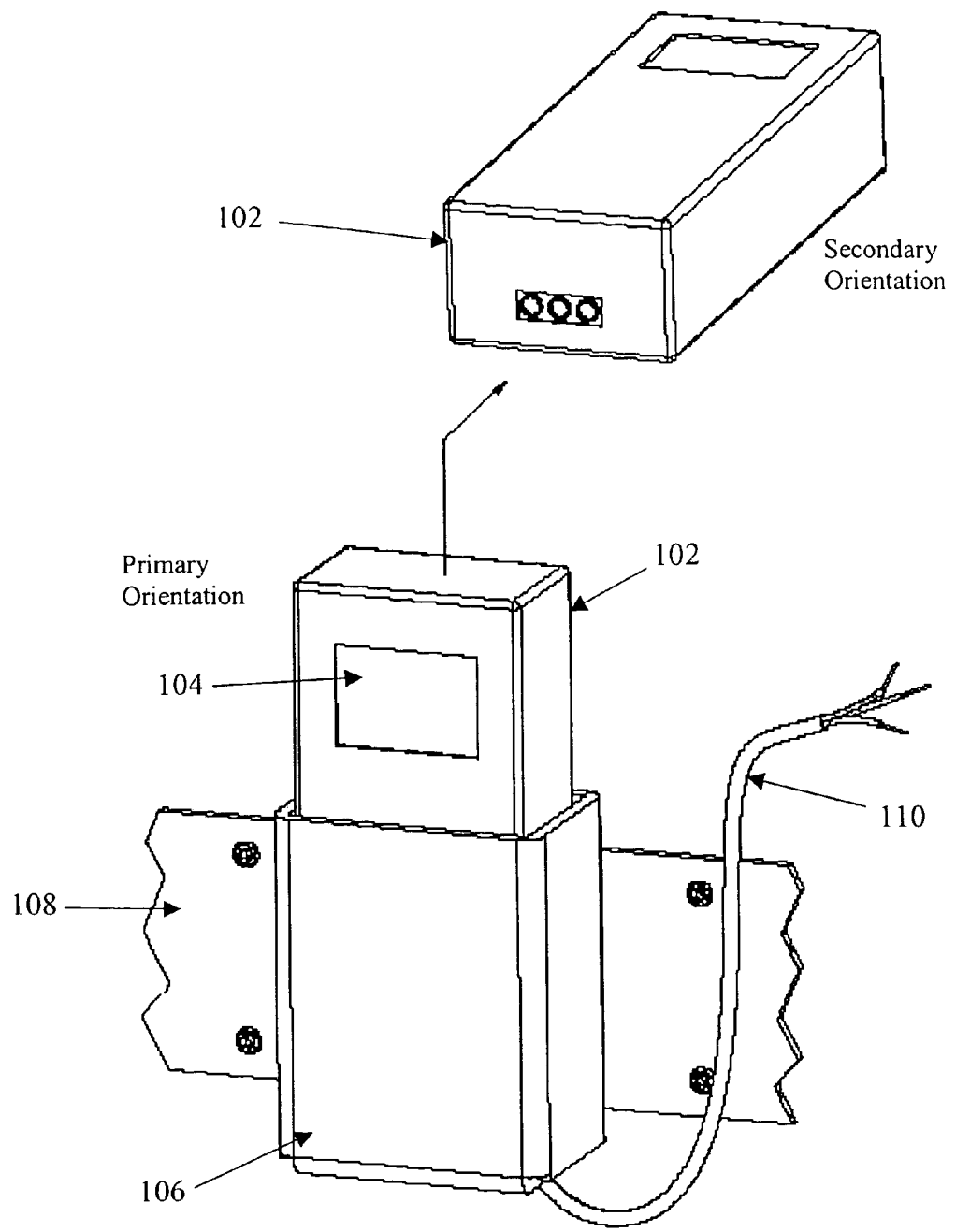
FIG. 1 is a diagram illustrating a navigation device having at least two modes of operations and functions according to one embodiment of the invention.

FIG. 1 is a diagram illustrating a navigation device having at least two modes of operations and functions according to one embodiment of the invention. According to one implementation of the invention, a navigation device 102 may include a display unit 104, for providing heading information to the user, a microprocessor, power source, compass and pedometer, or equivalent motion measuring algorithms. The device may be carried in a holster 106 which may be attached to a belt 108 around the user's waist. The holster or the navigation device 106 may include a communication interface with a link 110 to other devices, such as a computer, attached to the user. Such a link may be either wired or wireless.

The navigation device 102 may also include a communication port or contacts 109 such that, when it is placed within the holster 106, it is capable of communicating over the link 110 and sensing that it is in place in the holster. Such link 110 may be used to transmit data, control information, and other types of data or signals to and from the navigation device 106.

The navigation device 102 may have different functionality or modes of operation that may be manually or automatically triggered. For example, the navigation device 102 may be battery operated and may be worn by a user in a primary orientation, and also used in a secondary orientation, approximately perpendicular to the primary orientation.

In one implementation, the navigation device may have two modes of operation that automatically switched depending on some condition. For example, while the device 102 is affixed to the user in the primary orientation, the active functions may include dead reckoning navigation, azimuth indication, and personal orientation with respect to vertical indication. While the device 110 is in its secondary orientation, such as when it is hand-held approximately ninety (90) degrees from the primary orientation or no longer affixed to the user, the device ceases to perform dead reckoning and personal orientation functions yet continues to provide azimuth indication. Distinguishing between the primary and secondary orientations may be done in a number of ways. For instance, sensors within the navigation device 102 may indicate whether the device is in a horizontal orientation versus a vertical orientation. In another implementation, the device may change modes depending on whether it senses that it is placed in the holster 106 or out of the holster. This may be determined by detecting whether the navigation device is communicatively coupled to the link 110.

FIGS. 2–4 illustrate a navigation device 102 attached to a person 200 and that synchronizes its reference orientation with the orientation of the person 200. FIGS. 2 and 3 illustrate how a navigation device 102 is coupled around the person's waist using a coupling means such as a belt 108. In this illustration, the navigation device 102 is positioned along the person's back. FIG. 4 illustrates how the device can be used when the person 200 is in the crawling position.

In one implementation of the navigation device 102, sensors within the device 102 are configured to detect and/or distinguish between two user orientations. For example, the reference axis of an electronic compass within the navigation device 102 may be reconfigured depending on the position of the user 200. The device may have two or more internal reference axes (e.g., A, B, and C orthogonal axes) that can be reconfigured. For example, in one instance, the A & B axes may coincide with the horizontal plane (i.e., ground plane) and in a second instance, such as when the navigation device is rotated, the C & B axes may coincide with the horizontal plane. Thus, when the user 200 is standing upright (i.e., FIG. 2), the horizontal plane used as the reference for the electronic compass can be fixed to the axes of the device that are also horizontal (i.e., relative to the ground plane) when the user is standing upright. When the user 200 assumes a crawling position (i.e., FIG. 4), sensors within the device would detect the change in orientation and reassign the physical axes of the navigation device to coincide with the actual horizontal plane (i.e., the ground plane).

Figure 5:
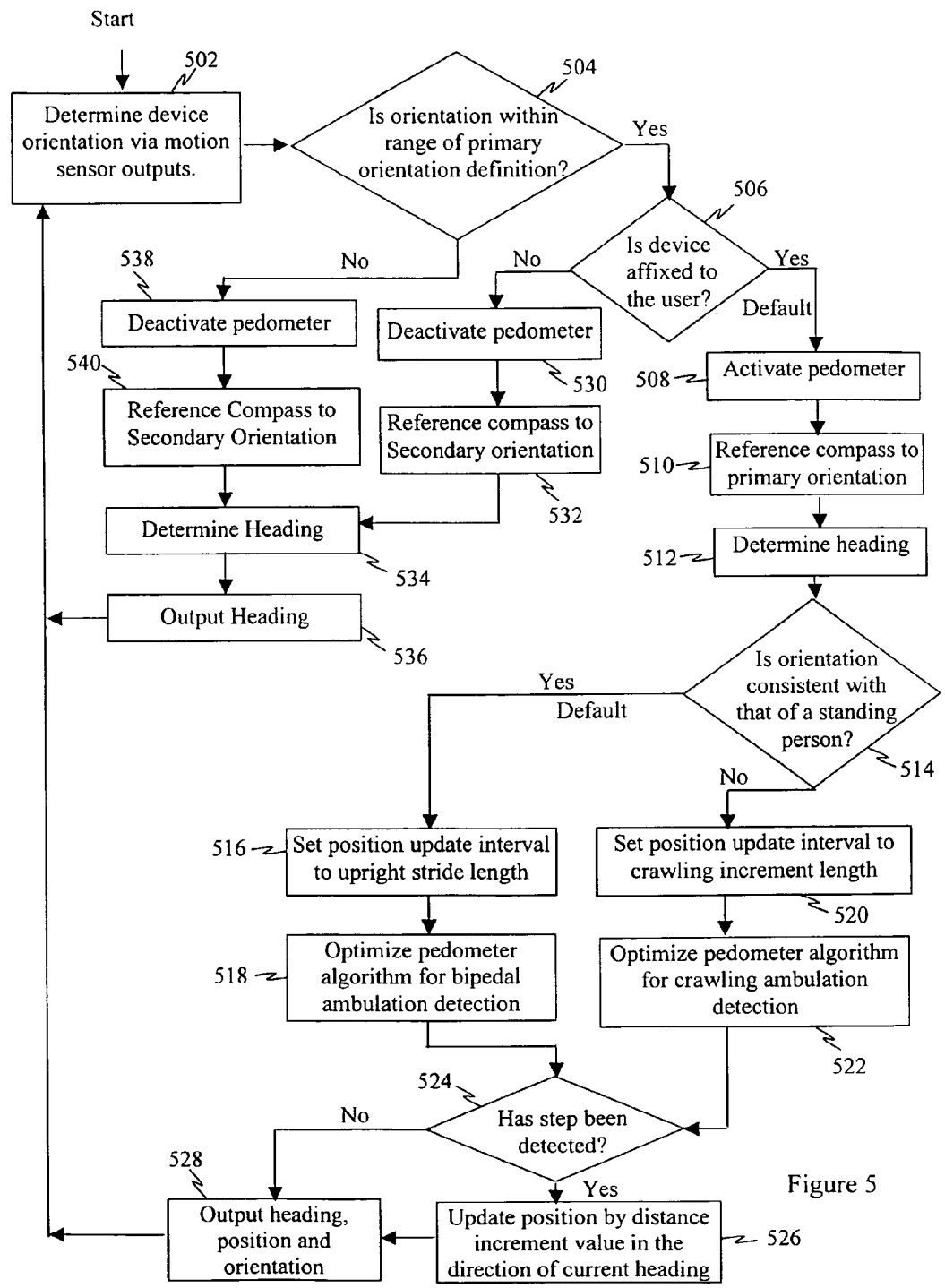
FIG. 5 is a flow diagram illustrating a method of function selection based upon device orientation according to one embodiment of the invention.

FIG. 5 is a flow diagram illustrating a method of function selection based upon device orientation according to one embodiment of the invention. This method may be executed by a microprocessor or processing unit that is an element of the device. While affixed to the user, the microprocessor within the device determines user orientation via motion values or signals, which may be obtained from one or more motion sensing devices 502, such as accelerometers and/or gyroscopes.

Figure 6:
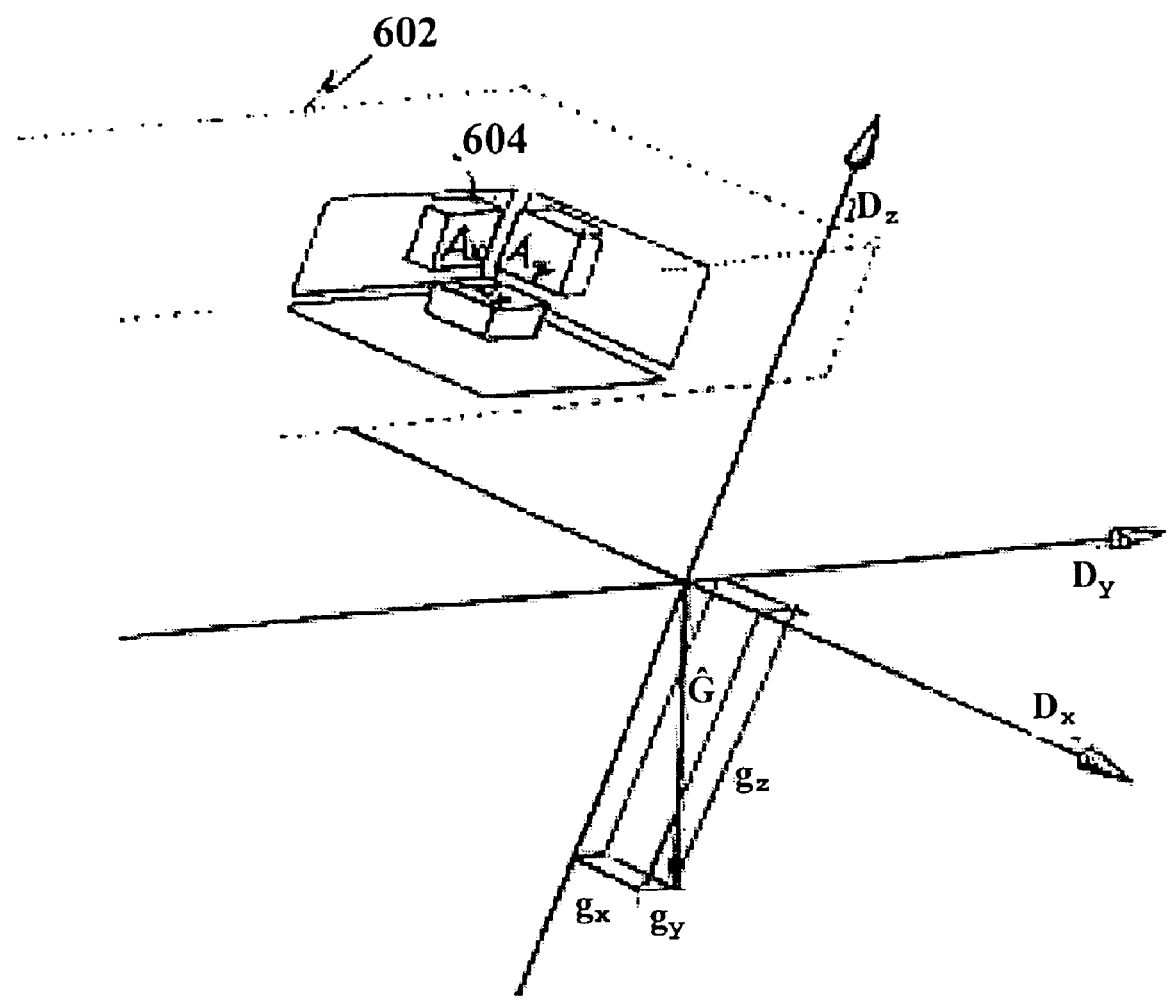
FIG. 6 illustrates one way in which orientation may be represented in one implementation of a navigation device with a plurality of motion sensing devices.

FIG. 6 illustrates one way in which orientation may be represented in one implementation of a navigation device 602 with a plurality of motion sensing devices 604, such as accelerometers and/or gyroscopes. The orientation is not reduced to a declination, but maintained in the vector format natural to the system such that the gravity vector $\hat{G}$ has components $g_x$, $g_y$, and $g_z$. These components are in the reference frame of the device 602 denoted by Dx, Dy, and Dz. The device 602 includes motion sensing devices Ax, Ay, and Az, 604 physically mounted with the sensitive axes placed orthogonally with respect to each other. The motion sensing devices 604 may be used for pedometry.

Referring again to FIG. 5, based on the one or more sensors, the device determines if its orientation is within the defined range of for a primary orientation 504. For instance, based on the magnitude of the sensor signals, a determination may be made if the orientation is more horizontal than vertical or vice versa. If it is determined that the device is in its primary orientation then a determination is may made whether the device is affixed to the user or holster 506. This may be done by determining if the device is coupled to a communication interface in the holster.

If it is determined that the device is in its primary orientation and affixed to the user or its holster, then a number of functions may be activated. For example, a pedometer or motion measuring algorithms may be activated. A compass may be reset or configured by referencing the compass horizontal plane to the physical axes of the device that are physically horizontal in the primary orientation 510. The heading may then be determined 512, for instance, by the direction indicated by the magnetic compass. A determination is made whether the orientation is consistent with a person in the standing positions 514. In one implementation of the invention, the direction of the gravity vector as sensed by the motion sensing devices (e.g., accelerometers and/or gyroscopes) defines the horizontal plane with respect to the physical axes of the device. In one implementation of the invention, such a device may use a triad of accelerometers and a triad of magnetometers, as illustrated in FIG. 6, so that equivalent measurements can be made in any orientation. If it is determined that the orientation is consistent with a person in the standing position, then the pedometer or motion measurement algorithms is configured to use a position update interval consistent with an upright stride length 516. The pedometer or motion measuring algorithms may then be optimized for bipedal ambulation detection 518. If on the other hand, the orientation of device is not consistent with a standing person, then the position update interval is set for a crawling increment length 520 and the pedometer or motion-measuring algorithm is optimized for crawling ambulation detection 522.

The device then determines if a step, either walking or crawling step, has been detected 524. If so, then position of the person is updated by the distance increment value (i.e., upright stride length or crawling increment length) in the direction of the current heading 526. The heading, position, and orientation is then outputted or provided to the user 528. The determination of orientation 502 is then started again.

If the device is not affixed to the user 506, then the pedometer or motion measuring algorithm may be deactivated 530 and the compass is referenced or reset according to the secondary orientation 532. The heading is then determined 534 and the heading is output to the user 536. The determination of orientation 502 is then started again.

If the orientation of the device is not within the range of the definition for the primary orientation 504, then the pedometer or motion measurement algorithm may be deactivated 538 and the compass is referenced to the secondary orientation 540. The heading is then determined 534 and the heading and position is output to the user 536. The determination of orientation 502 is then started again.

In one implementation of the invention, electronic or mechanical means of detecting the holster are provided. While the device is in the primary position, affixed to the user and in a secondary orientation relative to the gravity vector, the device is intended to register footsteps and body motion for the purposes of navigation, as when a person is walking. If the device is in the primary position, affixed to the user and in a first orientation relative to the gravity vector, the device is intended to register ground contact accelerations and body motion characteristic of a crawling human for the purposes of navigation, as would occur with a person on his hands and knees. The device functions are available via display or electronic signal to systems external to the device.

Figure 7:
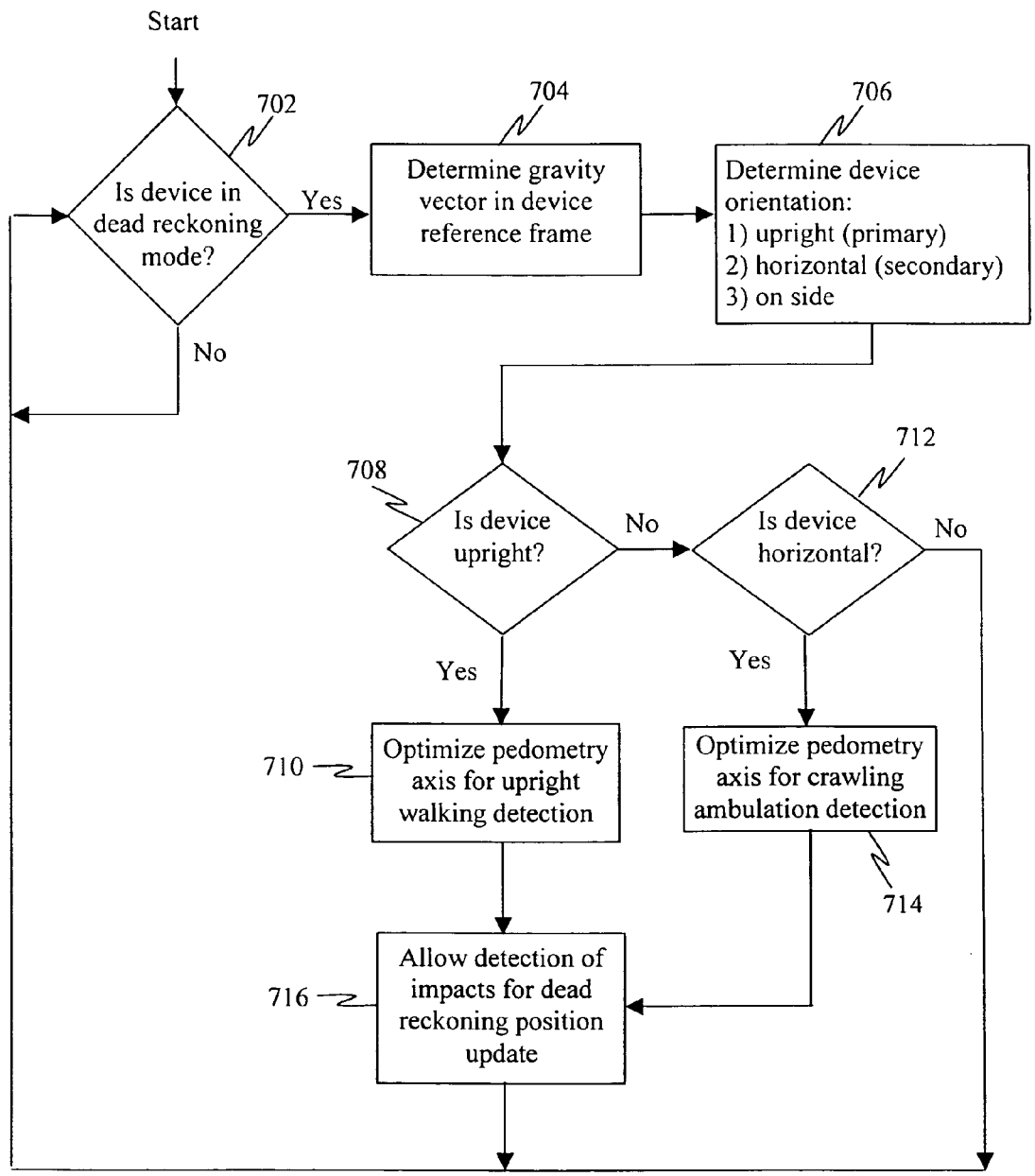
FIG. 7 is a flow chart illustrating a method of sensor selection and algorithm adaptation for the purpose of pedometry according to one implementation of an aspect of the invention.

FIG. 7 is a flow chart illustrating a method of sensor selection and algorithm adaptation for the purpose of human motion detection according to one implementation of an aspect of the invention. First, a determination is made of whether the navigation device is in a first mode of operation (i.e., dead reckoning mode) 702. If the device is not in the first mode of operation (i.e., dead reckoning mode) then the system keeps checking 702. Otherwise, if the device is operating in the first mode, a determination is made of the gravity vector (i.e., $\hat{G}$ in FIG. 6) relative to the device reference frame (i.e., Dx, Dy, and Dz in FIG. 6). This gravity vector is used to determine the orientation of the device, for instance, between upright, horizontal or on its side 706. If the device is upright 708, this can be interpreted as an indication that the user is standing up and the motion-measuring algorithm is optimized for detecting upright walking motions 710. If the device is determined to be horizontal 712, this can be interpreted as an indication that the user is in a crawling position and the motion-measuring algorithm is optimized for detecting crawling ambulation or motions 714. Once the device or algorithms have been optimized for detection of either walking or crawling motions, the system monitors user motions and updates the dead reckoning position when such motion is detected 716. The system then continues to monitor whether the device is in dead reckoning mode 702.

In various embodiments of the invention, the selection of a first or second algorithm includes selecting predetermined algorithms, adapting or configuring one or more algorithms for a particular type of operation.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications are possible. Those skilled, in the art will appreciate that various adaptations and modifications of the just described preferred embodiment can be configured without departing from the scope and spirit of the invention. Additionally, it is possible to implement embodiments of the invention or some of their features in hardware, programmable devices, firmware, software or a combination thereof. The invention or parts of the invention may also be embodied in a processor-readable storage medium or machine-readable medium such as a magnetic (e.g., hard drive, floppy drive), optical (e.g., compact disk, digital versatile disk, etc), or semiconductor storage medium (volatile and non-volatile). Therefore, it is to be understood that, within the scope of the appended claims, the invention may be practiced other than as specifically described herein.

What is claimed is:

1. A navigation device comprising:
   an electronic compass to detect an orientation and provide a corresponding heading signal;
   one or more motion sensing devices to detect motion along different axes and provide corresponding motion signals; and
   a processing unit communicatively coupled to the electronic compass and the one or more motion sensing devices to receive the heading signal and the one or more motion signals, determine a position and orientation, and automatically switch different navigation information On or Off depending on the orientation of the navigation device.

2. The navigation device of claim 1 wherein the processing unit is further configured to provide different navigation information depending on whether the navigation device is affixed to a user or not.

3. The navigation device of claim 2 further comprising:
   a visible indicator to provide navigation information to a user.

4. The navigation device of claim 1 wherein the navigation device automatically switches between different modes of operation depending on the orientation of the navigation device,
   and provides either heading or position information, depending on the mode of operation.

5. The navigation device of claim 1 wherein
   if the navigation device is affixed to a user and the device is in a primary orientation, navigation calculations are made according to bipedal ambulation to provide a position,
   if the navigation device is affixed to a user and the device is in a secondary orientation, then navigation calculations are made according to crawling ambulation to provide a position, and
   if the navigation device is hand-held, only azimuth data is provided to the user.

6. The navigation device of 5 wherein the electronic compass, the one or more motion sensing devices, and the processing unit are physically incorporated and housed in the navigation device.

7. The navigation device of claim 1 further comprising:
   a communication port to transmit navigation information.

8. The navigation device of claim 1 wherein the processing unit determines direction of a gravity vector from the one or more motion signals generated by the one or more motion sensing devices.

9. A method of navigation comprising:
   detecting whether the navigation device is inserted into a holster;
   obtaining an azimuth heading;
   calculating a dead reckoning position if the navigation device is inserted into the holster;
   providing the azimuth heading and dead reckoning position if the navigation device is inserted into the holster; and
   providing azimuth heading otherwise.

10. The method of claim 7 further comprising:
    determining an orientation of the navigation device relative to a horizontal plane;
    calculating the dead reckoning position according to bipedal ambulation when the navigation device is affixed to the user and is in a first orientation; and
    calculating the dead reckoning position according to crawling ambulation when the navigation device is affixed to the user and is in a second orientation.

11. A method comprising:
    determining the orientation of a navigation device relative to a horizontal plane;
    automatically selecting a first motion measurement algorithm if the navigation device is in a first orientation;
    automatically selecting a second motion measurement algorithm if the navigation device is in a second orientation; and
    providing a position according to the motion measurement algorithm selected;

automatically resetting the horizontal plane of reference to
- a first physical horizontal plane of the navigation device when the navigation device is in a first orientation, and
- a second physical horizontal plane of the navigation device when the navigation device is in a second orientation.

12. The method of claim 11 further comprising:
determining if the navigation device is affixed to a user;
automatically selecting the first motion measurement algorithm if the navigation device is in the first orientation and affixed to the user;
automatically selecting the second motion measurement algorithm if the navigation device is in the second orientation and affixed to the user; and
suspending all motion measurement calculations if the navigation device is not affixed to the user.

13. The method of claim 11 further comprising:
detecting if a step has been taken.

14. The method of claim 11 further comprising:
providing heading information.

15. A machine-readable medium having one or more instructions for dead reckoning navigation, which when executed by a processor, causes the processor to perform operations comprising
- detecting whether the navigation device is inserted into a holster;
- obtaining an azimuth heading;
- calculating a dead reckoning position if the navigation device is inserted into the holster;
- outputting the azimuth heading and dead reckoning position if the navigation device is inserted into the holster; and
- outputting the azimuth heading otherwise.

16. A computer-readable medium having one or more instructions for operating a navigation device, which when executed by a processor, causes the processor to perform operations comprising
- determining an orientation of the navigation device relative to a horizontal plane,
- calculating the dead reckoning position according to bipedal ambulation when the navigation device is affixed to the user and is in a first orientation,
- calculating the dead reckoning position according to crawling ambulation when the navigation device is affixed to the user and is in a second orientation; and
- resetting the horizontal plane of reference to
  - a first physical horizontal plane of the navigation device when the navigation device is in the first orientation, and
  - a second physical horizontal plane of the navigation device when the navigation device is in the second orientation.

17. A navigation device comprising:
an electronic compass to detect an orientation and provide a corresponding heading signal;
one or more motion sensing devices to detect motion alone different axes and provide corresponding motion signals;
a processing unit communicatively coupled to the electronic compass and the one or more motion sensing devices to receive the heading signal and the one or more motion signals, determine a position and orientation, and automatically provide different navigation information depending on the orientation of the navigation device; and
a detector to detect when the navigation device is inserted into a holster.

18. A navigation device comprising:
an electronic compass to detect an orientation and provide a corresponding heading signal, the electronic compass having a configurable horizontal plane that is
- set to a first physical horizontal plane of the navigation device when the navigation device is in a first orientation, and
- set to a second physical horizontal plane of the navigation device when the navigation device is in a second orientation;

one or more motion sensing devices to detect motion along different axes and provide corresponding motion signals; and
a processing unit communicatively coupled to the electronic compass and the one or more motion sensing devices to receive the heading signal and the one or more motion signals, determine a position and orientation, and automatically provide different navigation information depending on the orientation of the navigation device.

19. A method comprising:
determining the orientation of a navigation device;
automatically selecting a first motion measurement algorithm if the navigation device is in a first orientation;
automatically selecting a second motion measurement algorithm if the navigation device is in a second orientation;
determining a direction of a gravity vector from one or more motion signals generated by one or more motion sensing devices; and
providing a position according to the motion measurement algorithm selected.

* * * * *